(12) United States Patent
Ying et al.

(10) Patent No.: US 8,995,610 B2
(45) Date of Patent: Mar. 31, 2015

(54) CT SCANNING SYSTEMS AND METHODS USING MULTI-PIXEL X-RAY SOURCES

(75) Inventors: Zhengrong Ying, Belmont, MA (US); Sergey Simanovsky, Brookline, MA (US); Ram Naidu, Newton, MA (US); Sorin Marcovici, Lexington, MA (US)

(73) Assignee: Analogic Corporation, Peabody, MA (US)

( * ) Notice: Subject to any disclaimer, the term of this patent is extended or adjusted under 35 U.S.C. 154(b) by 442 days.

(21) Appl. No.: 13/060,778

(22) PCT Filed: Sep. 10, 2008

(86) PCT No.: PCT/US2008/075791
§ 371 (c)(1),
(2), (4) Date: May 23, 2011

(87) PCT Pub. No.: WO2010/030270
PCT Pub. Date: Mar. 18, 2010

(65) Prior Publication Data
US 2011/0211666 A1 Sep. 1, 2011

(51) Int. Cl.
*A61B 6/00* (2006.01)
*G01N 23/04* (2006.01)
(Continued)

(52) U.S. Cl.
CPC ............. *G01N 23/046* (2013.01); *A61B 6/032* (2013.01); *A61B 6/4028* (2013.01); *A61B 6/405* (2013.01);
(Continued)

(58) Field of Classification Search
CPC ...... A61B 6/032; A61B 6/035; A61B 6/4007; A61B 6/4014; A61B 6/54; H01J 35/065; H01J 35/06; H01J 35/08; H01J 2235/068; H01J 2235/062

USPC .............................. 378/4, 9, 15, 122, 124, 10
See application file for complete search history.

(56) References Cited

U.S. PATENT DOCUMENTS 5,625,661 A * 4/1997 Oikawa .......................... 378/15
7,627,081 B2 * 12/2009 Bontus .............................. 378/9
(Continued)

FOREIGN PATENT DOCUMENTS

DE 102006029198 11/2007
JP 64-062124 3/1989
(Continued)

OTHER PUBLICATIONS

International Search Report and the Written Opinion from corresponding PCT Application No. PCT/US2008/075791, Sep. 2009.
(Continued)

*Primary Examiner* — Jurie Yun
(74) *Attorney, Agent, or Firm* — McDermott Will and Emery LLP

(57) ABSTRACT

A CT scanning system may include a multi-pixel x-ray source, and a detector array. The multi-pixel x-ray source may have a plurality of pixels that are disposed along a z-axis, and that are sequentially activated so as to controllably emit x-rays in response to incident electrons. The detector array may have one or more rows of x-ray detectors that detect the x-rays that are emitted from the pixels and have traversed an object, and generate data for CT image reconstruction system. In third generation CT scanning systems, the number of detector rows may be reduced. Multi-pixel x-ray source implementation of saddle curve geometry may render a single rotation single organ scan feasible. Using a multi-pixel x-ray source in stationary CT scanning systems may allow x-ray beam design with a minimal coverage to satisfy mathematical requirements for reconstruction.

10 Claims, 6 Drawing Sheets

(51) Int. Cl.
   *A61B 6/03* (2006.01)
   *A61B 6/02* (2006.01)
(52) U.S. Cl.
   CPC .............. *A61B 6/466* (2013.01); *A61B 6/482* (2013.01); *A61B 6/027* (2013.01); *A61B 6/4007* (2013.01); *G01N 2223/419* (2013.01)
   USPC ............................................................ 378/9

(56) References Cited

U.S. PATENT DOCUMENTS

| | | | |
|---|---|---|---|
| 7,760,849 B2 | 7/2010 | Zhang | |
| 2002/0094064 A1 | 7/2002 | Zhou et al. | |
| 2005/0111610 A1 | 5/2005 | De Man et al. | |
| 2005/0190878 A1 | 9/2005 | DeMan et al. | |
| 2005/0226364 A1 | 10/2005 | De Man et al. | |
| 2006/0045234 A1 | 3/2006 | Pelc et al. | |
| 2010/0296624 A1 * | 11/2010 | Bontus et al. | 378/4 |

FOREIGN PATENT DOCUMENTS

| | | |
|---|---|---|
| JP | 2005237972 | 9/2005 |
| JP | 2005288152 | 10/2005 |
| JP | 2009-512481 | 3/2009 |
| JP | 2009-519471 | 5/2009 |
| WO | WO2006/090323 | 8/2006 |
| WO | 2007/046036 | 4/2007 |
| WO | 2007/070580 | 6/2007 |
| WO | WO2008/027706 | 3/2008 |
| WO | WO2008/047308 | 4/2008 |

OTHER PUBLICATIONS

Xu et al., "A Tetrahedron Beam Computed Tomography Benchtop System with a Multiple Pixel Field Emission X-Ray Tube," Medical Physics, 38:5500-5508 (2011).
Zhang et al., "Tetrahedron Beam Computed Tomography (TBCT): A New Design of Volumetric CT System,"Phys. Med. Biol. 54:3365-3378 (2009).
Office Action dated May 16, 2013 from Corresponding Japanese Patent Application No. 2011-526836.
Office Action dated Feb. 27, 2014 from Corresponding Japanese Application No. 2011-526836.

* cited by examiner

CT SCANNING SYSTEMS AND METHODS USING MULTI-PIXEL X-RAY SOURCES

BACKGROUND

With the recent advancement in multi-pixel x-ray sources, for example based on carbon nanotube field emission technology, new scanning geometries may be designed to balance the cost between multi-pixel x-ray tubes and the combination of detector array and data acquisition electronics.

Recently, new scanning geometries have been proposed to improve image quality for single rotation, single organ scans. However, the proposed implementations of these new geometries cumbersome or impractical. For example, a saddle curve scanning geometry was proposed to be implemented by tilting gantry or table. It is impractical, however, to tilt the table back and forth when scanning the patient, and it is also mechanically difficult to tilt the gantry back and forth while the gantry is rotating at high speed. Stationary CT (and tomosynthesis) scanning systems have the advantage of low maintenance cost compared to the conventional rotating scanning systems. It is difficult, however, to realize such as a system using an electron beam scanning source.

Accordingly, there is a need for CT scanning systems and methods that have improved geometries and provide improved image quality, using multi-pixel x-ray sources.

SUMMARY

A CT scanning system for generating a CT image of an object may include a multi-pixel x-ray source, a detector array, and an image reconstruction system. The multi-pixel x-ray source may include a plurality of pixels disposed along a z-axis and adapted to be sequentially activated, each pixel configured to controllably emit x-rays in response to incident electrons, when activated. The detector array may include one or more rows of x-ray detectors that are configured to detect x-rays that are emitted from the pixels and that have traversed the object, and to generate data from detected x-rays. The image reconstruction system configured to generate the CT image of the object from the data generated by the x-ray detectors.

In one embodiment, the CT system may be a third generation CT system, In this embodiment, the detector array may have a number of detector rows that is reduced compared a CT scanning system that has a single pixel x-ray source and provides same x-ray beam coverage along the z-axis.

In one embodiment, each pixel may be configured to have x-ray beam coverage of the entire detector array, when activated, and the CT scanning system may be a multi-detector row CT scanning system that implements a saddle curve trajectory for a single rotation, single organ scan.

In one embodiment, the CT system may be a stationary CT scanning system, for which a multi-pixel x-ray source may allow x-ray beam design with a minimal coverage to satisfy mathematical requirements for reconstruction.

DETAILED DESCRIPTION

Figure 1:
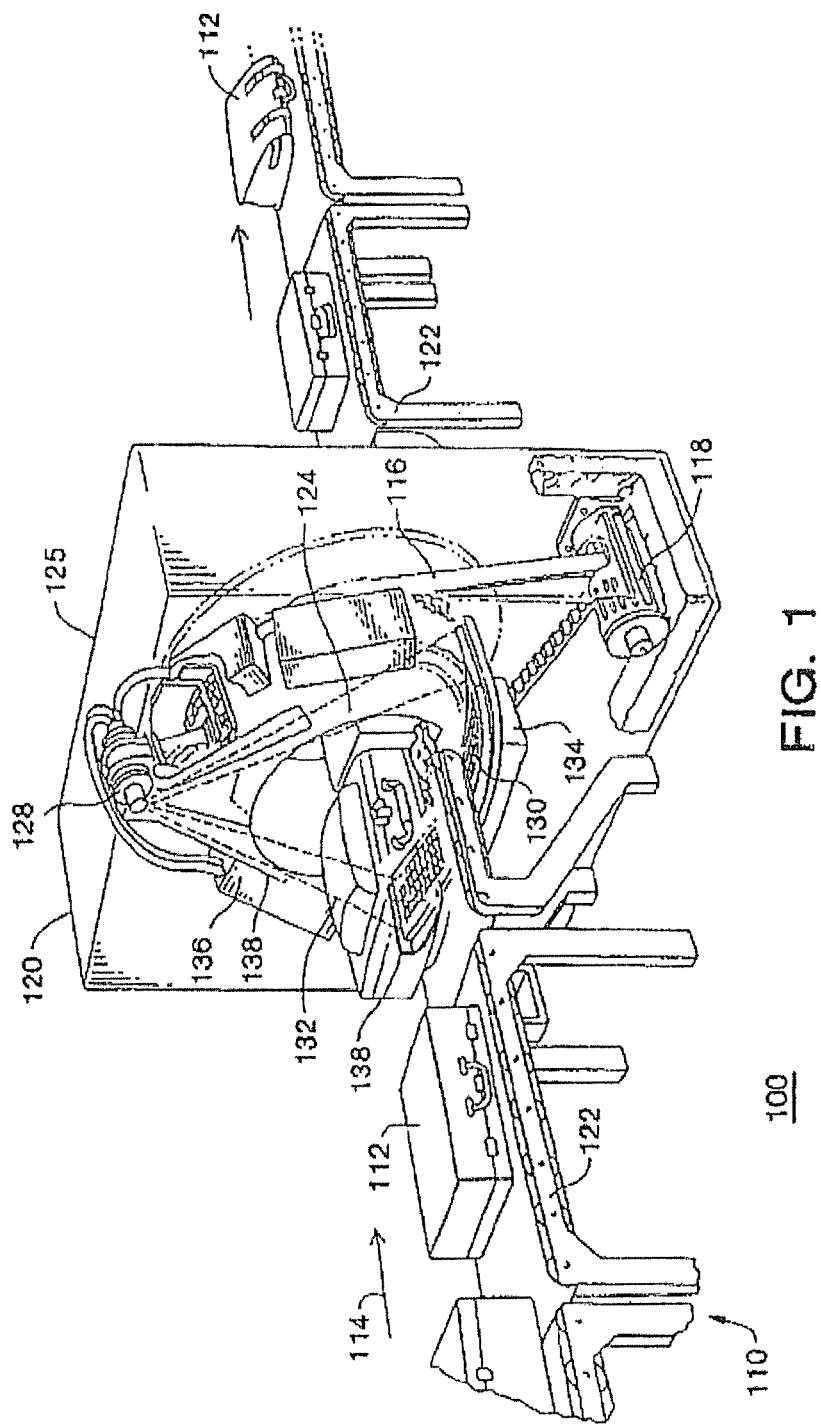
FIG. 1 is a perspective view of a CT scanning system including a multi-pixel x-ray source, which can be adapted to incorporate the system and perform method described herein.

In the present disclosure, CT (computed tomography) scanning systems and methods are described that use multi-pixel x-ray sources.

In computed tomography, cross-sectional images of an object are reconstructed by collecting and integrating a plurality of x-ray projection data from different projection angles. In a typical CT system, x-rays emitted from an x-ray source pass through a portion of the target object, and are detected by a detector array. The portion of the object is irradiated from many different directions, for example by rotating the x-ray source and a detector array around the object. In a spiral (or helical) CT system, the x-ray source together with the detector array rotates continuously as the object is moved through the x-ray scan field, so that a continuous set of projection data is obtained for the entire region scanned.

The detector array measures the intensity of the x-ray beam that has traversed a portion of the object being scanned, which may be an anatomical region of a patient, for example, or a piece of baggage being scanned at an airport. The portion of the material that is irradiated by an x-ray beam attenuates the beam by absorbing and/or scattering the x-rays. The imaged quantity is thus the spatial distribution of the attenuation coefficient inside a region of interest within the irradiated portion of the object. Various calibrations and corrections are performed to calibrate and correct the imaged quantity to approximate physical properties of the scanned materials, such as mass density and atomic number of the scanned materials. The detector array generates data indicative of the attenuated intensities of the x-rays that have traversed the material, digitizes them, and transmits the digitized detection signals to an image reconstruction system.

The image reconstruction system implements reconstruction algorithms and other image processing techniques, known in the art, to generate a CT image of the object, either slice by slice or volume by volume. In helical CT scanning, different reconstruction algorithms are known in the art such as Nutating Slice Reconstruction (the "NSR") algorithm (described in U.S. Pat. No. 5,802,134). Recent advances in the reconstruction algorithms allow improvement of image quality when a scanning geometry generates projection data that satisfy the completeness conditions for exact reconstruction as used in A. Katsevich. "Theoretically exact FBP-type inversion algorithm for spiral CT," *SIAM J. Appl. Math.*, 62 (6): 2012-2026, 2002 (the "Katsevich") and Kudo, H., Noo, F., and Defrise, M., "Quasi-exact filtered backprojection algorithm for long-object problem in helical cone-beam tomography," IEEE TRANSACTIONS ON MEDICAL IMAGING, VOL. 19, NO. 9, pp. 902-921, SEPTEMBER 2000 (the "Kudo"). These references are incorporated herein by reference in their entirety.

Conventional x-ray sources may include, for example, a thermionic x-ray tube, which produce x-rays by accelerating electrons through an electric field. A conventional thermionic x-ray tube typically includes an electron source (or cathode) for generating electrons, and an x-ray target (or anode) containing x-ray emissive material adapted to emit x-rays in response to incident electrons that have been accelerated by an accelerating electric field. The electric field may be established by means of a voltage provided to the x-ray ray source by a high voltage power supply. X-rays are generated due to the interaction of the accelerated electrons with the electrons and the nuclei that make up the atoms of the target material. The generated x-rays radiate from a spot on the x-ray target (or anode), commonly called the focal spot.

These conventional x-ray sources are single-pixel x-ray sources that produce a single beam of x-rays from a single location. Recently, multi-pixel x-ray sources have been developed, which generate x-rays from a plurality of locations. In a multi-pixel x-ray source, x-ray beams are generated from different origins or locations within the x-ray target.

One example of such multi-pixel x-ray sources is the multi-pixel x-ray tube based on carbon nanotube field emission technology. A multi-pixel x-ray source based on carbon nanotube field emitters is described in "A multi-beam x-ray imaging system based on carbon nanotube field emitters," Medical Imaging 2006: Physics of Medical Imaging, edited by Michael J. Flynn and Jiang Hsieh, Proceedings of SPIE Vol 6142, 614204 (2006). This reference is incorporated herein by reference in its entirety.

Other examples of multi-pixel x-ray sources include, but are not limited to: multiple anodes (i.e. x-ray targets) with a single cathode, wherein x-rays are generated from a plurality of locations by sweeping one electron beam sequentially through each of the multiple anodes that are all structured within one single vacuum enclosure; multiple cathodes, each of which generate beams of electrons that hit different spots on a single anode and all of which are housed within a single vacuum enclosure; and a plurality of x-ray tubes that are housed within a single housing structure with each individual tube having its own vacuum enclosure.

In the present disclosure, CT scanning systems and methods that use multi-pixel x-ray sources are described. Improved scanning geometry, enhanced image quality, and reduced manufacturing or maintenance cost may result.

Figure 2:
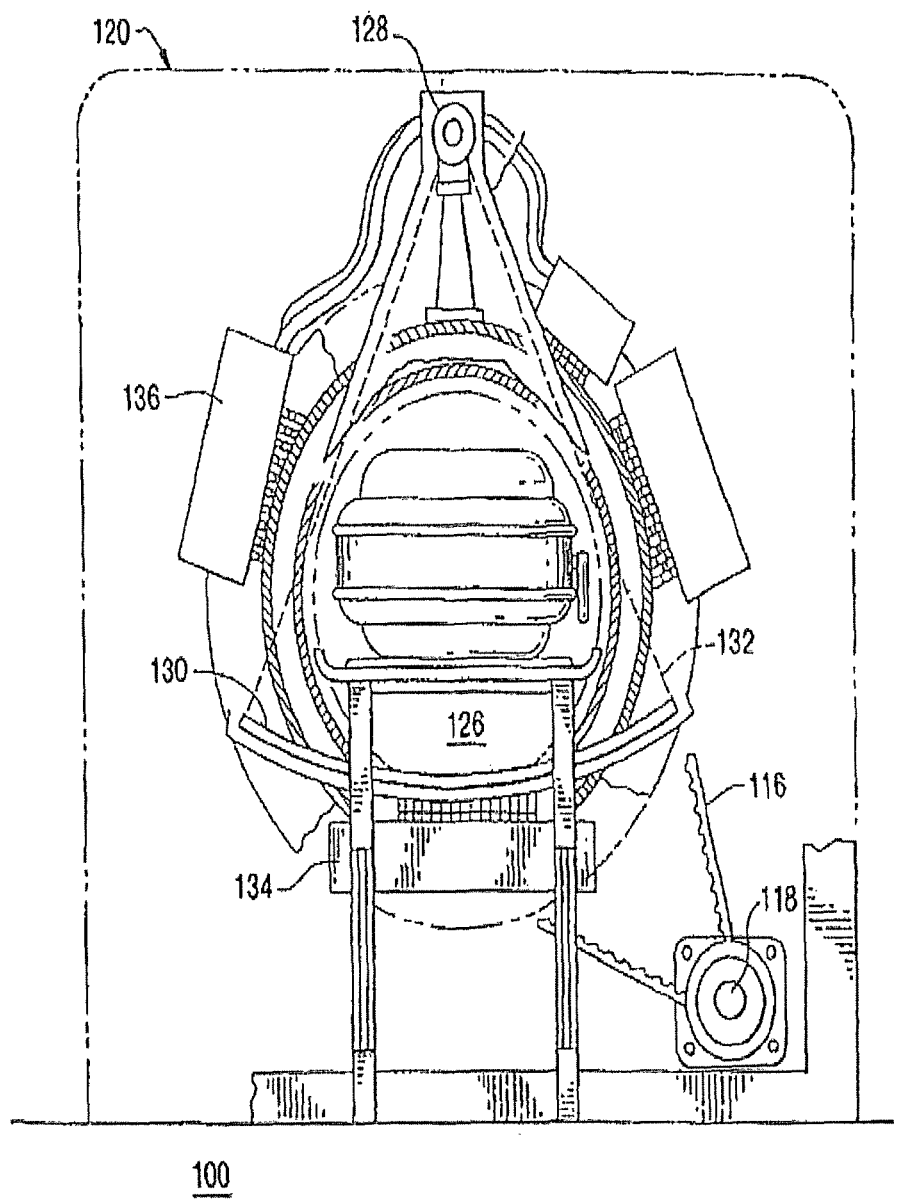
FIG. 2 is a cross-sectional end view of the system of FIG. 1.
Figure 3:
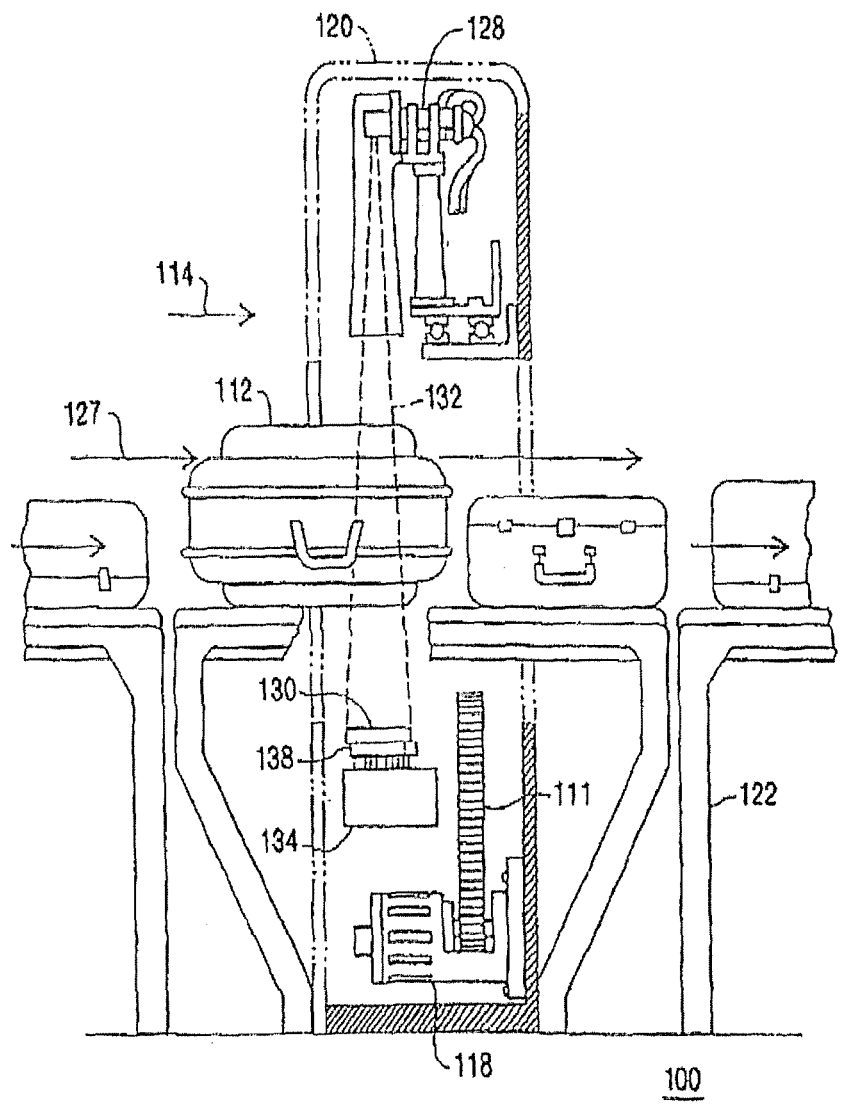
FIG. 3 is a cross-sectional radial view of the system of FIG. 1.

Referring to the drawings, FIGS. 1, 2 and 3 show perspective, end cross-sectional and radial cross-sectional views, respectively, of one embodiment of a CT scanning system incorporating a multi-pixel x-ray source including at least two pixels, each pixel configured and arranged so as to emit x-rays in response to incident electrons, each pixel separately controllable so as to generate x-rays independently of one another.

The CT scanning system 100 may include a conveyor system 110 for continuously conveying an object 112 in a direction indicated by arrow 114 through a central aperture of a CT scanning system 120. In the illustrated embodiment, the object 112 is a baggage or luggage. The conveyor system may include motor driven belts for supporting the baggage. Conveyer system 110 is illustrated as including a plurality of individual conveyor sections 122; however, other forms of conveyor systems may be used.

The CT scanning system 120 may include an annular shaped rotating platform, or disk, 124 disposed within a gantry support 125 for rotation about a rotation axis 127 (shown in FIG. 3) that is preferably parallel to the direction of travel 114 of the baggage 112. Disk 124 is driven about rotation axis 127 by any suitable drive mechanism, such as a belt 116 and motor drive system 118, or other suitable drive mechanism, such as the one described in U.S. Pat. No. 5,473,657 issued Dec. 5, 1995 to Gilbert McKenna, entitled "x-ray Tomographic Scanning System," which is assigned to the present assignee and, which is incorporated herein in its entirety by reference. Rotating platform 124 defines a central aperture 126 through which conveyor system 110 transports the baggage 112. A z-axis is defined as the conveyor moving direction or the axis that is perpendicular to the rotating platform when scanning without any movement of the conveyor system.

The system 120 includes a multi-pixel x-ray source 128, an embodiment of which is described more fully below, and a detector array 130. The multi-pixel x-ray source 128 and the detector array 130 are disposed on diametrically opposite sides of the platform 124. The detector array 130 may include one or more rows of detectors.

The system 120 further includes a data acquisition system (DAS) 134 for receiving and processing signals generated by detector array 130, and an x-ray tube control system 136 for supplying power to, and otherwise controlling the operation of x-ray tube 128. The system 120 is also preferably provided with a computerized system (not shown) for processing the output of the data acquisition system 134 and for generating the necessary signals for operating and controlling the system 120. The computerized system can also include a monitor for displaying information including generated images. System 120 also includes shields 138, which may be fabricated from lead, for example, for preventing radiation from propagating beyond gantry 125.

As described more fully hereinafter, the multi-pixel x-ray source 128 includes at least two separate, spaced-apart pixels, from which separately controlled x-ray beams can be independently created and generated. These beams, shown generally at 132 in FIGS. 1-3, pass through a three dimensional imaging field, through which conveying system 110 transports baggage 112. After passing through the baggage disposed in the imaging field, detector array 130 can receive each beam 132. The detector array then generates signals representative of the densities of exposed portions of the object 112. The beams 132 therefore define a scanning volume of space.

Platform 124 rotates about its rotation axis 127, thereby transporting x-ray source 128 and detector array 130 in circular trajectories about the object 112 as the conveyor system 110 continuously transports the object through central aperture 126, so as to generate a plurality of projections at a corresponding plurality of projection angles. When multi-energy scanning mode is configured, the control system 136 separately controls the application of different voltages to each of the pixels of the x-ray tube 128. The detector array 130 then receives data corresponding to different energy levels of x-ray spectra at various projection angles.

Figure 4:
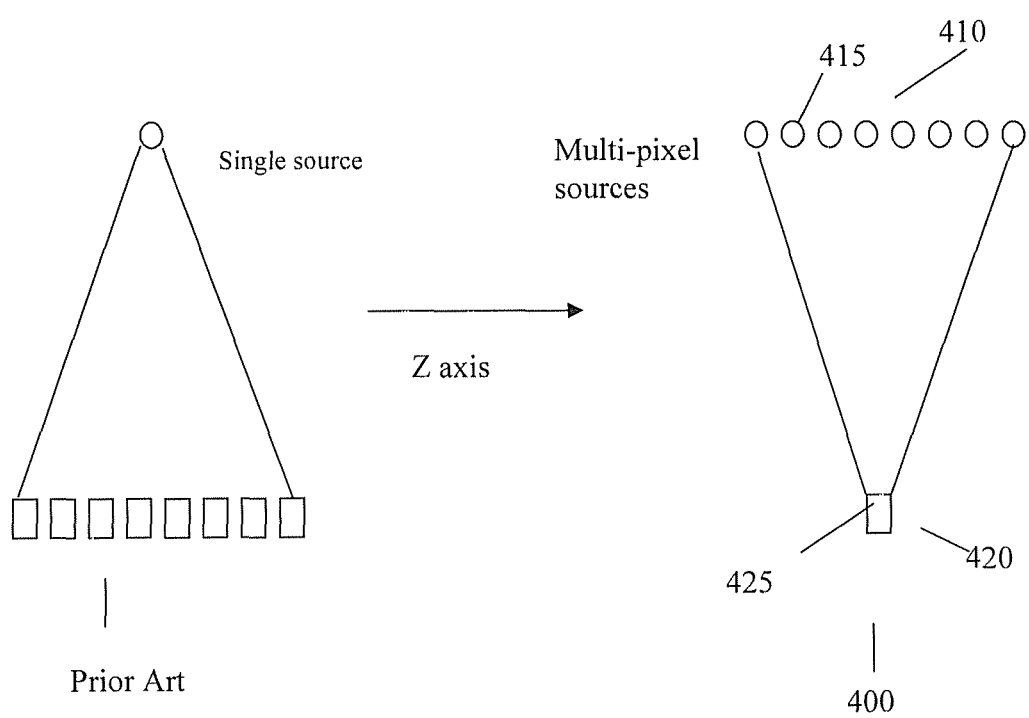
FIG. 4 is a conceptual block diagram of a third generation helical CT scanning system that has a reduced number of detector rows while obtaining the same Z coverage, by using a multi-pixel x-ray tube.

FIG. 4 is a conceptual block diagram of a CT scanning system 400, in accordance with one embodiment of the present disclosure. The CT scanning system uses a multi-pixel x-ray source to reduce the number of rows of x-ray detectors, while providing the same x-ray beam coverage along the z-axis (or axis of rotation).

The CT scanning system 400 may be a third generation helical or spiral CT system, in which the x-ray source and the detector array are attached to a freely rotating gantry. In a conventional helical CT system, a table translates a patient (or other object) smoothly during a scan through the scanning system along the axis of rotation (z-axis), so that the x-ray beam traces out a helical path with respect to the scanned patient (or other object). In such a conventional helical CT system, slip rings may be used to transfer power and data on and off the rotating gantry, and a switched mode power supply may be used that is powerful enough to supply the X-ray tube, but small enough to be installed on the gantry.

In the illustrated embodiment, the CT scanning system 400 includes a multi-pixel x-ray source 410. The multi-pixel x-ray source 410 includes a plurality of pixels 415 disposed along the z-axis. Each one of the pixels in the source 410 is sequentially activated. When activated, each pixel controllably emits x-rays in response to incident electrons. In one embodiment of the present disclosure, the multi-pixel x-ray source may include one or more carbon nanotube field emission x-ray tubes. The carbon nanotube field emission x-ray tube may include multiple carbon nanotube field emission cathodes, each of which provides one pixel of electron beam targeting at one anode location to generate one pixel of x-ray beam.

In another embodiment of the present disclosure, the multi-pixel x-ray source may include one or more carbon nanotube field emission x-ray tubes. The carbon nanotube field emission x-ray tube may include multiple carbon nanotube field emission cathodes, each of which provides one pixel of electron beam targeting at one anode location to generate one pixel of x-ray beam.

In another embodiment of the present disclosure, the multi-pixel x-ray source may include a plurality of vacuum enclosures, each of which includes an anode and a cathode and each of which is a pixel of the x-ray source. In other words, in this embodiment the multi-pixel x-ray source may include a plurality of x-ray tubes that are housed within a single housing structure, each individual x-ray tube having its own vacuum enclosure.

The CT scanning system 400 further includes a detector array 420. The detector array 420 includes one or more rows of x-ray detectors 425. The x-ray detectors detect x-rays that are emitted from the pixels and that have traversed the object, and generate data (pertaining to a spatial distribution of the attenuation coefficients of the x-rays that have traversed an axial slice of the object) from detected x-rays. An image reconstruction system (not shown) generates a CT image of the object using the data generated by the x-ray detectors.

The CT scanning system 400 includes a gantry or support (not shown) for the multi-pixel x-ray source and the detector array. The support rotates the source and the detectors array about the z-axis while the object is being scanned.

The CT scanning system 400 may be further include a controller that sequentially activates the pixels. The controller controls the timing of the sequential activation of the pixels, i.e. sequentially activates the plurality of pixels in accordance with a timing sequence. The controller also controls the duration, intensity and energy level of x-ray emission by each one of the pixels.

In one embodiment, the controller may be further configured to sequentially activate the plurality of pixels so as to substantially achieve a same x-ray beam coverage along the z-axis and to generate similar data coverage for a helical reconstruction algorithm that is used in the image reconstruction system, compared to the x-ray beam coverage along the z-axis and the data coverage achieved by a multi-detector row CT helical scanning system that has a single pixel x-ray source.

Because a multi-pixel x-ray source is used in the illustrated embodiment, instead of a single-pixel x-ray source, the number of detector rows in the detector array can be reduced compared to multi-detector row CT scanning systems that employ a single pixel x-ray source with multiple rows of detectors to provide the same x-ray beam coverage along the z-axis. Such multi-pixel source and single detector row configuration reduce the scatter effect across different detector rows, which occur in conventional multi-detector row CT scanning systems that employ a single pixel x-ray source.

In the embodiment illustrated in FIG. 4, the CT scanning system 400 includes a single row of x-ray detectors, and the multi-pixel x-ray source includes a plurality N of pixels. The CT scanning system 400 provides the same x-ray beam coverage along the z-axis per rotation, compared to a multi-detector row CT scanning system having N rows of x-ray detectors and a single pixel x-ray source. Conventional third generation helical CT scanning employs one source with multiple rows of detectors, as shown on the left hand side of FIG. 4. In the embodiment illustrated in FIG. 4, a multi-pixel x-ray source 410 is used. The number of detector rows can be reduced, (for example to a single row of detectors, as illustrated on the right hand side of FIG. 4), with the same x-ray beam coverage along the z-axis per rotation.

In this way, one source with multi-row N detector array scanning system, such as N=24 rows, can be configured into multi-pixel N x-ray sources, such as N=24 pixels, with one row of detectors. In other embodiments, the detector array includes a number N1 of rows of x-ray detectors, and the multi-pixel x-ray sources includes a plurality N2 of pixels, where N1×N2=N. In these embodiments, the CT scanning system is adapted to provide same x-ray beam coverage along the z-axis as a multi-row detector CT scanning system having a single pixel x-ray source and N rows of x-ray detectors. In other words, different embodiments of the present disclosure may used any different combinations of the factors of N for the number of x-ray sources $N_1$ and the number of rows of detectors $N_2$ may be used, such that $N=N_1 \times N_2$; for example, $N_1=8$, $N_2=3$.

In these configurations, x-ray pixel activation timing and the spacing of the detector rows are configured so that the same x-ray beam coverage, compared to a multi-row detector CT scanning system having a single pixel x-ray source, is assured. Large spacing between adjacent detector rows or adjacent x-ray pixels can be configured to yield the same x-ray beam coverage along the z-axis, compared to a multi-detector row CT helical scanning system that has a single pixel x-ray source, and to generate similar data coverage for a helical reconstruction algorithm that is used in the image reconstruction system.

A method of reducing the number of x-ray detector rows in a detector array in a CT scanning system, without affecting x-ray beam coverage along a z-axis during a rotation of the x-ray source and the detector array, is disclosed. The method may include providing a multi-pixel x-ray source having a plurality N1 of pixels, and a number N2 of rows of x-ray detectors. The method may further include sequentially activating the pixels along a direction substantially parallel to the z-axis, so as to provide same x-ray coverage as a CT scanning system having a single pixel source and a plurality M of rows of x-ray detectors, where M=N1×N2.

Image quality improvements with the latest multi-detector row CT scanning systems, for example a 320-slice CT scanning system, can also be made using a multi-pixel x-ray tube to increase the coverage along the z-axis for single rotation single organ scanning applications, which may include but are not limited to cardiac imaging and liver imaging. In this way, the data can satisfy the completeness condition for exact reconstruction.

Figure 5:
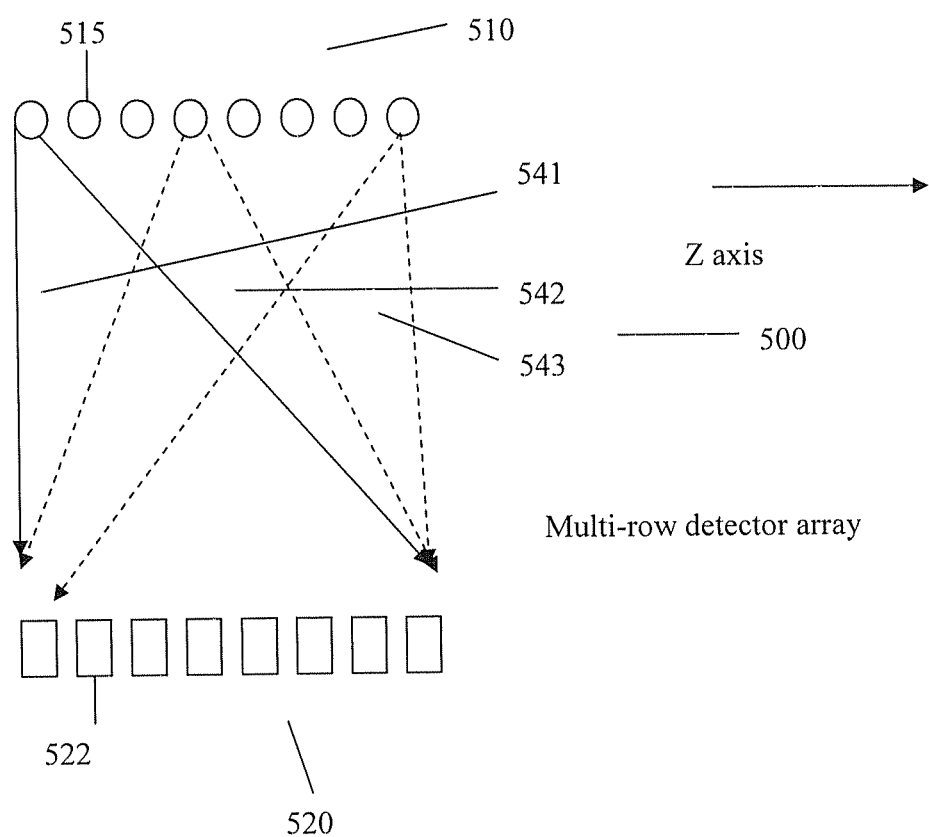
FIG. 5 is a conceptual block diagram of a multi-detector row CT scanning system that uses a multi-pixel x-ray tube to increase Z coverage for a single rotation single organ scanning application.

FIG. 5 is a conceptual block diagram of an improved multi-detector row CT scanning system 500 that uses a multi-pixel x-ray source, in accordance with another embodiment of the present disclosure. The improved multi-detector row CT scanning system 500 uses a multi-pixel x-ray source to increase the coverage along the z-axis for a single rotation single organ CT scanning application, for example cardiac CT imaging and liver imaging.

The CT system 500 includes a multi-pixel x-ray source 510. The multi-pixel x-ray source 510 including a plurality of pixels 515 disposed along a z-axis. Each pixel can be sequentially activated, to controllably emit x-rays in response to incident electrons.

The CT system 500 further includes a detector array 520 that has a plurality of rows of x-ray detectors 522, i.e. the detector array 520 is a 2D (two dimensional) array. The detectors 522 in the detector array 520 are configured to detect x-rays that are emitted from the pixels and that have traversed the object, and to generate data from detected x-rays. An image reconstruction system (not shown) generates a CT image of the object from the data generated by the x-ray detectors. The CT scanning system 500 may further include a gantry support (not shown) for the multi-pixel x-ray source and the detector array, which rotate the multi-pixel x-ray source and the detector array about the z-axis while the object is being scanned.

The CT scanning system 500 may further include a controller (not shown) that sequentially activates the pixels, and controls timing of the sequential activation of the pixels, as well as duration and intensity of the x-ray beams emitted by the by pixels.

As shown e.g. by reference numerals 541, 542, and 543 in FIG. 5, each pixel 515 in the multi-pixel x-ray source is configured to have x-ray coverage of the entire detector array, when activated. In one embodiment, such configurations of the coverage for each x-ray pixel may be made by using a multi-slit collimator. In other words, each pixel of the x-ray source has x-ray coverage of the whole detector array at one time, and the control of the x-ray source can be made for one rotation of data such that the completeness condition of the data is satisfied for image reconstruction, thereby improving image quality.

In the embodiment illustrated in FIG. 5, the controller controls the pixels in the multi-pixel x-ray source in such a way that a complete set of data is generated for the image reconstruction system by the detectors in the detector array, during a 360 degree rotation of the multi-pixel x-ray source 510 and the detector array.

A method of enhancing image quality in a single rotation single organ CT scan may include providing a multi-pixel x-ray source having a plurality of pixels, and a detector array including a plurality of rows of x-ray detectors, where each pixel in the multi-pixel x-ray source has x-ray beam coverage of the entire detector array, when the pixel is activated. The method may further include rotating the multi-pixel x-ray source and the detector array about the z-axis while the object is being scanned. The method may further include sequentially activating the pixels so that each activated pixel controllably emits x-rays in response to incident electrons, in a way that a complete set of data is generated for an image reconstruction system by the detectors in the detector array, during a 360 degree rotation of the multi-pixel x-ray source and the detector array about a z-axis.

In one embodiment, the controller may activate the pixels in the multi-pixel x-ray source in such a way as to implement a saddle trajectory scanning geometry for the multi-pixel x-ray source, without having to tilt the translational table (or conveyor) or the rotating gantry. For example, the implementation of saddle-like trajectory proposed by Pack et al. 2004 can be made by using a multi-pixel x-ray source, without tilting table or gantry. Saddle trajectories for CT imaging is described for example in Jed D Pack, Frederic Noo, and H Kudo, "Investigation of saddle trajectories for cardiac CT imaging in cone-beam geometry," Phys. Med. Biol, 49 (2004) 2317-2336 (the "Pack reference"). The Pack reference is incorporated herein by reference in its entirety.

In this embodiment, the controller may be further configured to activate the pixels in the multi-pixel x-ray source in such a way as to implement a scanning geometry in which a saddle trajectory is implemented for the multi-pixel x-ray source, and in which neither the x-ray source, nor the detector array, nor the scanned object engages in any motion along the z-axis during scanning.

As described in the Pack reference, a two-dimensional detector array (including multiple detector rows) may be used to collect a 2D set of data for the image reconstruction system, while the x-ray source moves along a given trajectory relative to the object being scanned. The data generated by the detectors pertain to the spatial distribution of the attenuation coefficient of x-rays inside the region of interest in the object. As described in the Pack reference, for an exact reconstruction of such a spatial distribution of attenuation coefficients, both the source trajectory and the detector array must satisfy certain constraints. Given a specific source trajectory, the detector array 520 must be wide enough to provide complete data for the reconstruction of the region of interest in the object being scanned.

The following mathematical definition of a saddle trajectory is provided in the Pack reference. In an x-y-z Cartesian coordinate system, consider two arbitrary functions, f(x) and g(y) that are twice continuously differentiable and satisfy all of the following conditions:

$$f''(x)>0 \text{ everywhere}; f'(0)=0; f(0)<0; \text{ and}$$

$$g''(y)<0 \text{ everywhere}; g'(0)=0; g(0)=-f(0).$$

Then a saddle trajectory is defined as the curve at the intersection of surfaces S1 and S2, where S1 and S2 are defined as follows:

$$S1=\{(x,y,z):z=f(x)\} \text{ and}$$

$$S2=\{(x,y,z):z=g(y)\}.$$

The surfaces S1 and S2, the intersection of which defines the saddle trajectory, are thus defined from appropriate functions f(x) and g(y).

In one embodiment of the present disclosure, a saddle trajectory may be mathematically parametrized by using the following special function for saddle curve implementation:

$$\alpha(\lambda)=[R \cos \lambda, R \sin \lambda, h \cos 2\lambda],$$

where $\alpha(\lambda)$ is the source trajectory, $\lambda$ is the view angle, R is the source to isocenter distance, and h is the half distance of the multi-pixel x-ray source coverage in Z. $h \cos 2\lambda$ specifies which x-ray pixel has to be turned on with respect to the view angle when $h \cos 2\lambda$ is discretized. The improved CT scanning system described above using multi-pixel x-ray source can obtain projection data satisfying completeness conditions for exact image reconstruction without requiring the x-ray sources, detector arrays, tables, and/or patients engage in any motion along the z-axis.

A method of implementing a saddle trajectory in a CT system without tilting a rotational gantry or conveyor may include providing a multi-pixel x-ray source having a plurality pixels, and a detector array including a plurality of rows of x-ray detectors, where each of the pixels is constructed and arranged to have x-ray coverage of the entire detector array, when the pixel is activated. The method may further include rotating the multi-pixel x-ray source and the detector array about the z-axis while the object is being scanned. The method may further include sequentially activating the pixels so that each activated pixel controllably emits x-rays in response to incident electrons, in a way that data completeness conditions for an exact reconstruction algorithm that is used in the image reconstruction system are satisfied. For example one or more exact reconstruction algorithms described in Katsevich, Sudo, or Pack, can be used to improve the image quality of the scan, during a 360 degree rotation of the multi-pixel x-ray source and the detector array about a z-axis.

In stationary CTs, creative geometries may take advantage of multi-pixel x-ray sources as well. Because there is no rotation involved with a stationary CT scanning system, the beam-line can be designed in different shapes to fit to space constraints, where the scanning system is to be placed (checkpoint of airports, by way of example). Also, the CT image reconstruction only requires 180° of the x-ray beam coverage for every point within the field scan of view. For traditional third generation CTs, this translates to the minimal acquisition of 180°+ fan angle. With a multi-pixel x-ray source, on the other hand, mathematical requirements can be satisfied with a beam-line configuration as illustrated in FIG. 6.

Figure 6:
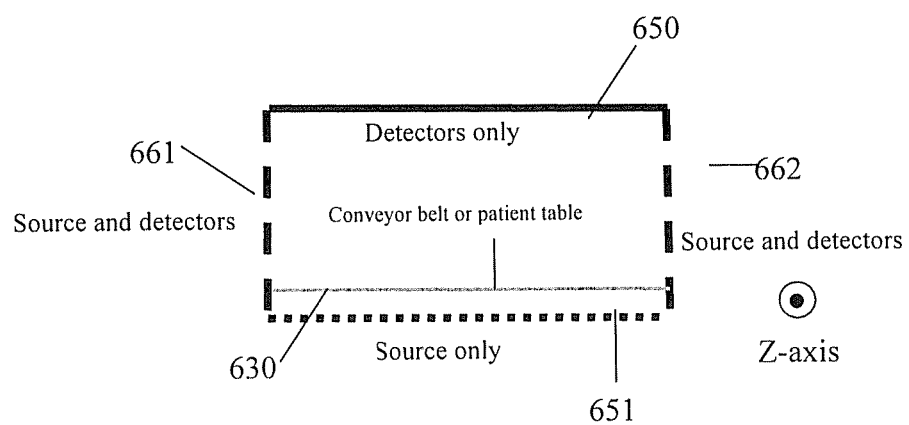
FIG. 6 is a conceptual block diagram of a beam line for a stationary CT system using a multi-pixel x-ray source.

FIG. 6 is a conceptual block diagram of a beam line for a stationary CT system 600 that uses a multi-pixel x-ray source. The CT system 600 may include a rectangular opening for screening checked baggage or carry-on baggage at airports. The CT system 600 may include a multi-pixel x-ray source, and a detector array that does not rotate with respect to the multi-pixel x-ray source. The CT system 600 may further include a conveyor 630 configured to translate the object along the z-axis (perpendicular to the rectangular opening) during the scan. The CT system 600 may further include a controller (not shown) that controls the timing, intensity, and duration of the x-ray emission by the pixels in the multi-pixel x-ray source.

The CT system 600 may further include an image reconstruction system (not shown), which is configured to generate the CT image of the object from the data generated by the x-ray detectors, while only requiring 180 degrees of x-ray beam coverage for every point within the scan field of view.

As illustrated in FIG. 6, the beam line of the CT system is configured and arranged so that only the detector array is disposed along one side of the rectangular opening 650, and only the multi-pixel x-ray source is disposed along another side of the rectangular opening 651 on the opposite side to 650.

Along the other two sides 661 and 662 of the rectangular opening, both the multi-pixel x-ray source and the detector array are disposed. When these two sides of the x-ray sources and detectors are not present, the beam-line reduces to a stationary tomosynthesis scanning system.

A stationary CT scanning system with a multi-pixel x-ray source may thus allow x-ray beam design with a minimal coverage to satisfy mathematical requirements for image reconstruction. The stationary CT scanning system does not require a rotating gantry, and projection data corresponding to different view angles is acquired by controlling the sequential activation timing of each pixel of x-ray source, which is disposed along the three sides of the rectangular opening of the scanning system.

In summary, CT systems and methods have been described that include multi-pixel x-ray sources for improved scanning geometry, enhanced image quality, and reduced manufacturing or maintenance cost The systems and methods described above may allow the number of detector rows for third generation CT scanning systems to be reduced, thereby reducing cost for detector arrays and DAS (data acquisition systems). Multi-pixel x-ray tube implementation of a saddle curve geometry, or other geometries that satisfy data completeness conditions for exact reconstruction, may render single rotation single organ scans with improved image quality, without any part of the scanning system or the scanned patient being involved in any motion along the z-axis. Stationary CT scanning systems with multi-pixel x-ray tubes may allow x-ray beam designs with a minimal coverage to satisfy mathematical requirements for image reconstruction. In this way, space efficiency may be obtained for special applications such as carry-on baggage screening at checkpoints in airports.

In these claims, reference to an element in the singular is not intended to mean "one and only one" unless specifically so stated, but rather "one or more," All structural and functional equivalents to the elements of the various embodiments described throughout this disclosure that are known or later come to be known to those of ordinary skill in the art are expressly incorporated herein by reference, and are intended to be encompassed by the claims. Moreover, nothing disclosed herein is intended to be dedicated to the public, regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A CT scanning system for generating a CT image of an object, the system comprising:
   a multi-pixel x-ray source including a plurality of pixels disposed along a z-axis and operative to be sequentially activated, each pixel operative to controllably emit x-rays in response to incident electrons, when activated;
   a detector array including one or more rows of x-ray detectors, the detectors operative to detect x-rays that are emitted from the pixels and that have traversed the object, and to generate data from detected x-rays;
   wherein each pixel is operative, when activated, to produce x-ray beam coverage of the entire detector array;
   an image reconstruction system operative to generate the CT image of the object from the data generated by the x-ray detectors; and
   a support for the multi-pixel x-ray source and the detector array, the support operative to rotate the source and the detector array about the z-axis while the object is being scanned by the CT scanning system;
   wherein the multi-pixel x-ray source and the detector rows are positionable and the sequential activation of the multi-pixel x-ray source is controllable; and
   wherein the sequential activating implements a scanning geometry in which a saddle trajectory is implemented for the multi-pixel x-ray source, and in which neither the x-ray source, nor the detector array, nor the scanned object engages in any motion along the z-axis during scanning.

2. The CT scanning system of claim 1, wherein the CT scanning system is a third generation helical CT scanning system.

3. The CT scanning system of claim 1, further comprising a controller configured to sequentially activate the pixels, the controller further configured to control timing of the sequential activation of the pixels, as well as duration, intensity, and energy level of x-ray emission by each one of the pixels.

4. The CT scanning system of claim 1, wherein the multi-pixel x-ray source is a carbon nanotube field emission x-ray tube; and wherein the carbon nanotube field emission x-ray tube comprises multiple carbon nanotube field emission cathodes, each of which provides one pixel of electron beam targeting at one anode location to generate one pixel of x-ray beam.

5. The CT scanning system of claim 1, wherein the multi-pixel x-ray source comprises a plurality of vacuum enclosures, each of which comprises an anode and a cathode and each of which is a pixel of the x-ray source.

6. The CT scanning system of claim 1, wherein the multi-pixel x-ray source comprises a plurality of cathodes, and a single anode within one vacuum enclosure.

7. A CT system configured to generate a CT image of an object, the CT system comprising:
a multi-pixel x-ray source including a plurality of pixels disposed along a z-axis, each pixel operative to be sequentially activated and to controllably emit x-rays in response to incident electrons, when activated;
a detector array comprising a plurality of rows of x-ray detectors, the detector array stationary with respect to the multi-pixel x-ray source in a direction parallel to the z-axis, the detectors operative to detect x-rays that are emitted from the pixels and that have traversed the object, and to generate data from detected x-rays;
an image reconstruction system operative to generate the CT image of the object from the data generated by the x-ray detectors;
wherein each pixel is operative, when activated, to produce x-ray beam coverage of the entire detector array;
a support for the multi-pixel x-ray source and the detector array, the support constructed and arranged so as to rotate the multi-pixel x-ray source and the detector array about the z-axis while the object is being scanned; and
a controller operative to sequentially activate the pixels, the controller further operative to control timing of the sequential activation of the pixels, as well as duration, intensity and energy level of x-ray emission by each one of the pixels; wherein the sequential activating implements a scanning geometry in which a saddle trajectory is implemented for the multi-pixel x-ray source, and in which neither the x-ray source, nor the detector array, nor the scanned object engages in any motion along the z-axis during scanning.

8. The CT system of claim 7, wherein the controller is further configured to control the pixels in the multi-pixel x-ray source so that data completeness conditions for an exact reconstruction algorithm that is used in the image reconstruction system is satisfied.

9. The CT system of claim 7, wherein a mathematical parameterization of the saddle trajectory comprises:

$$\alpha(\lambda)=[R \cos \lambda, R \sin \lambda, h \cos 2\lambda],$$

wherein $\alpha(\lambda)$ is the source trajectory, $\lambda$ is the view angle, R is the source to isocenter distance, and h is the half distance of the multi-pixel x-ray source coverage along the z-axis, and wherein $h \cos 2\lambda$ specifies the source activation timing with respect to the view angle $\lambda$.

10. A method of enhancing image quality in a single rotation single organ CT scan, the method comprising:
providing a multi-pixel x-ray source having a plurality pixels disposed along a z-axis, and a detector array including a plurality of rows of x-ray detectors; wherein each pixel is operative, when activated, to have x-ray coverage of the entire detector array;
rotating the multi-pixel x-ray source and the detector array about the z-axis while an object is being scanned; and
sequentially activating the pixels so that each activated pixel controllably emits x-rays in response to incident electrons, in a way that data completeness conditions for an exact reconstruction algorithm that is used in an image reconstruction system are satisfied; wherein sequentially activating the pixels implements a scanning geometry in which a saddle trajectory is implemented for the multi-pixel x-ray source, and in which neither the x-ray source, nor the detector array, nor the scanned object engages in any motion along the z-axis during scanning.

* * * * *